United States Patent [19]
Cole

[11] Patent Number: 6,162,182
[45] Date of Patent: Dec. 19, 2000

[54] PRESSURE TIP CANNULA

[75] Inventor: James E. Cole, Ventura, Calif.

[73] Assignee: Becton, Dickinson and Company, Franklin Lakes, N.J.

[21] Appl. No.: 09/140,156

[22] Filed: Aug. 26, 1998

[51] Int. Cl.$^7$ .................................................. A61B 5/00
[52] U.S. Cl. ............................................. 600/486; 600/488
[58] Field of Search .................................. 600/486, 488, 600/561

[56] References Cited

U.S. PATENT DOCUMENTS

| | | | |
|---|---|---|---|
| 2,981,911 | 4/1961 | Warnick | 600/488 |
| 3,038,465 | 6/1962 | Allard et al. | 600/488 |
| 4,456,013 | 6/1984 | De Rossi et al. | 600/488 |
| 4,548,205 | 10/1985 | Armeniades et al. | 600/488 |
| 4,554,927 | 11/1985 | Fussell | 128/670 |
| 4,672,974 | 6/1987 | Lee | 600/486 |
| 4,771,782 | 9/1988 | Millar | 600/488 |
| 4,886,070 | 12/1989 | Demarest | 128/675 |
| 5,050,297 | 9/1991 | Metzger | 600/486 |
| 5,181,516 | 1/1993 | Sato et al. | 128/673 |

FOREIGN PATENT DOCUMENTS

WO 90/06723  6/1990  WIPO ........................ A61B 5/0215

*Primary Examiner*—Robert L. Nasser
*Attorney, Agent, or Firm*—Eric M. Lee, Esq.

[57] ABSTRACT

A cannula that is usable to remove blood from a patient during an operation such as bypass surgery where the cannula has a pressure sensor in the form of an electronic piezoresistive chip located at or adjacent the location within the heart where the blood is being removed. The crystal has a sensing side and a reference side that is exposed to a reference pressure that is known. The piezoresistive chip is mounted at the distal end of the cannula such that its sensing side faces outwardly away from the central bore of the cannula that is transporting the blood that is being removed and thus is isolated from the dynamic effects of the moving blood. In addition, the pressure sensor has a characteristic drift based on temperature and the sensor is therefore standardized at body temperature, 36 degrees Centigrade, so that the pressure sensor is standardized at the temperature at which it will be used when positioned within the patient. As such, the pressure sensor is zeroed at the body temperature and is more accurate in measuring pressure.

2 Claims, 4 Drawing Sheets

PRESSURE TIP CANNULA

BACKGROUND

This invention relates to a special cannula that is usable during heart by-pass surgery and where the cannula is capable of being employed to remove blood directly from the heart while at the same time, provide a device to continuously monitor the pressure within the heart during that blood removal.

In carrying out various procedures that require a heart bypass operation, blood is removed directly from the patient's heart and to do so, a cannula is introduced into the left side of the heart i.e. from the left ventricle or atrium where the blood is pumped away and then reintroduced into the heart through the right side of the heart, typically via the ascending aorta. The blood is pumped from the heart by means of a special pump, one of which is the Jarvik heart pump and which pulls the blood from the left heart and replaces the blood back into the right heart. A cannula is therefore placed with its distal end into the particular chamber of the patient's heart and which sucks the blood from that chamber. The cannula is generally a very large device to be capable of relatively large flows of blood and, as an example, can be of the size of 24 to 28 French. Since the cannula is directly introduced into the heart to withdraw the blood, it is obviously of extreme importance that the pressure in the heart chamber not become negative, that is, where the heart chamber could collapse from the over-removal of the blood. The danger is that the blood will be removed at such a high rate of flow that the heart itself will be sucked dry. Accordingly, in heart bypass procedures, a pressure transducer is used to maintain an internal constant monitor of the pressure of the blood within the heart chamber as it is being removed. As such, therefore, the pressure transducer can even, if desired, have control of the pump and slow down the pump in the event the pressure within the heart chamber is reduced to a predetermined pressure, approaching a negative value, and which assures that the negative pressure is not reached within the heart.

In current devices, a liquid filled column is used and which is introduced into the heart adjacent the location of the distal end of the cannula that is removing the blood. There are, however, several drawbacks to the use of a liquid filled column in determining the pressure of the blood in the heart chamber. As one difficulty, the tip of the liquid filled catheter or tube containing the liquid can become occluded if it presses against the inner heart wall and therefore will not read the correct pressure in the heart. In addition, the transducer that is attached to the catheter or tube and which is external of the patient, must be positioned at the heart level at all times. Since the pressures being measured in the heart are so low, the error that will be caused by not having the transducer at the exact level can be critical, that is, a difference of one inch in position of the transducer below the level of the heart will indicate 2 mmHg. higher than the actual pressure and such a difference is considerable when taking into account that the pressures measured in the heart may approach 0 mmHg. and, as stated, it its critical that the pressure remain positive.

One type of pressure sensor that has been used in a patient to monitor pressure, for example, is the pressure tip cannula where an electrical sensor, in the form of a electronic chip, is located at the distal end of the catheter or cannula and which is positioned at the location where the pressure is desired to be determined. In such sensors, the chip is a piezoresistive crystal that is positioned between the chamber where the pressure is being measured and a chamber having a know reference pressure, such as atmospheric pressure. As the chip flexes in response to changes in pressure, its resistance changes and that change in resistance is sensed by a Wheatstone bridge and a electronic instrument converts the changes in resistance into measurements of pressure. Such devices have been used for a variety of purposes, such as intrauterine pressure transducers and the like, however the use of such a transducer within a chamber in the patient's heart during a bypass operation requires extreme accuracy since the pressures involved are extremely low, i.e. a few mmHg. In addition, it is critical that the pressure in the chamber of the heart where the blood is being withdrawn not be negative. Accordingly, as the cannula is sucking blood from the interior of the patient's heart, it is necessary to deal with extremely low pressures since there is a real danger in the event the pressure becomes negative in the chamber where the blood is being pumped out yet the accuracy must be extremely precise due to the critical nature of the operation and the well being of the patient.

One problem associated with the use of pressure tip transducers is that they can be affected by the moving flow of liquid moving past the transducer itself. As previously explained, due to the low pressures being measured and the need for extremely high accuracy, any affect that could alter the accuracy of the instrument is critical. With the use of a large cannula that is withdrawing blood at a fairly large flow, therefore, it is important that the piezoresistive chip transducer not be affected by the dynamics of the flow. For example, if the pressure sensitive side of the chip is exposed to the flowing blood, the blood tends to draw the chip in the direction of flow and therefore the pressure readings may be less than the actual pressure that is present within the heart chamber. In addition, it is important that the chip itself not block or in any way hinder the flow of the blood as it is being withdrawn from the heart and therefore must be positioned in a special location to avoid such problem. The use of a chip in such a situation also raises the problem that the piezoresistive chip must be operable even when contacting one of the internal walls of the heart.

Another possible source of inaccuracies in such pressure tip monitor cannulas is the electrical sensor, located at the distal end of the cannula, has an inherent temperature drift and which causes a zero drift change due to a temperature change, that is, as the temperature changes, the sensor will experience a drift in its zero reading. While the presence of that drift may be acceptable when dealing with the higher pressures involved in the normal blood pressure of a patient, the same temperature drift can introduce an unacceptable inaccuracy into the pressure monitoring system at the range of pressures encountered in the heart chamber during the bypass operation.

SUMMARY OF THE INVENTION

The present devices use a continuous pressure monitor where an electronic piezoresistive sensor is located at the distal end of a cannula that withdraws the blood from a chamber of the left heart, typically the left ventricle of the atrium. The cannula is of the order of a 24 to 36 French cannula and the sensor itself is positioned at the distal end of the cannula in a position so as to not obstruct the flow of blood into the cannula from the patient's heart. The sensor is standardized at the temperature of the body, that is, the patient's temperature, so as to eliminate the zero drift characteristic of the sensor and to insure that the sensor is reading as accurately as possible. By standardizing the sensor at the body temperature, 36 degrees C, the sensor, when placed in the heart chamber, will provide as zero reading at 0 mmHg. pressure and therefore any changes of pressure, even at such low pressures, will be sensed accurately from that zero reading. Accordingly, the pressure in the heart chamber can be monitored with great precision even at the low pressures present in the heart chamber to assure the pressure does not become negative and cause damage to the heart.

In addition, with the particular positioning of the electrical sensor within the cannula, the dynamics of the flowing blood through the cannula do not affect the accuracy of the piezoresistive sensor. The piezoresistive chip is positioned such that its sensing side does not face the flow of the blood as it passes through the cannula from the heart and thus is unaffected and isolated from the dynamics of that flow and its accuracy therefore not affected by that flow of blood. As a further feature of the particular location of the sensor, the sensor provides an accurate reading even if the distal end of the cannula contacts the internal wall of the heart.

The above and other advantages and features of the present invention will be apparent in the following detailed description of the preferred embodiment when read in conjunction with the appended drawings wherein the same reference numerals denote the same or similar parts throughout the several views.

DETAILED DESCRIPTION OF THE INVENTION

Figure 1:
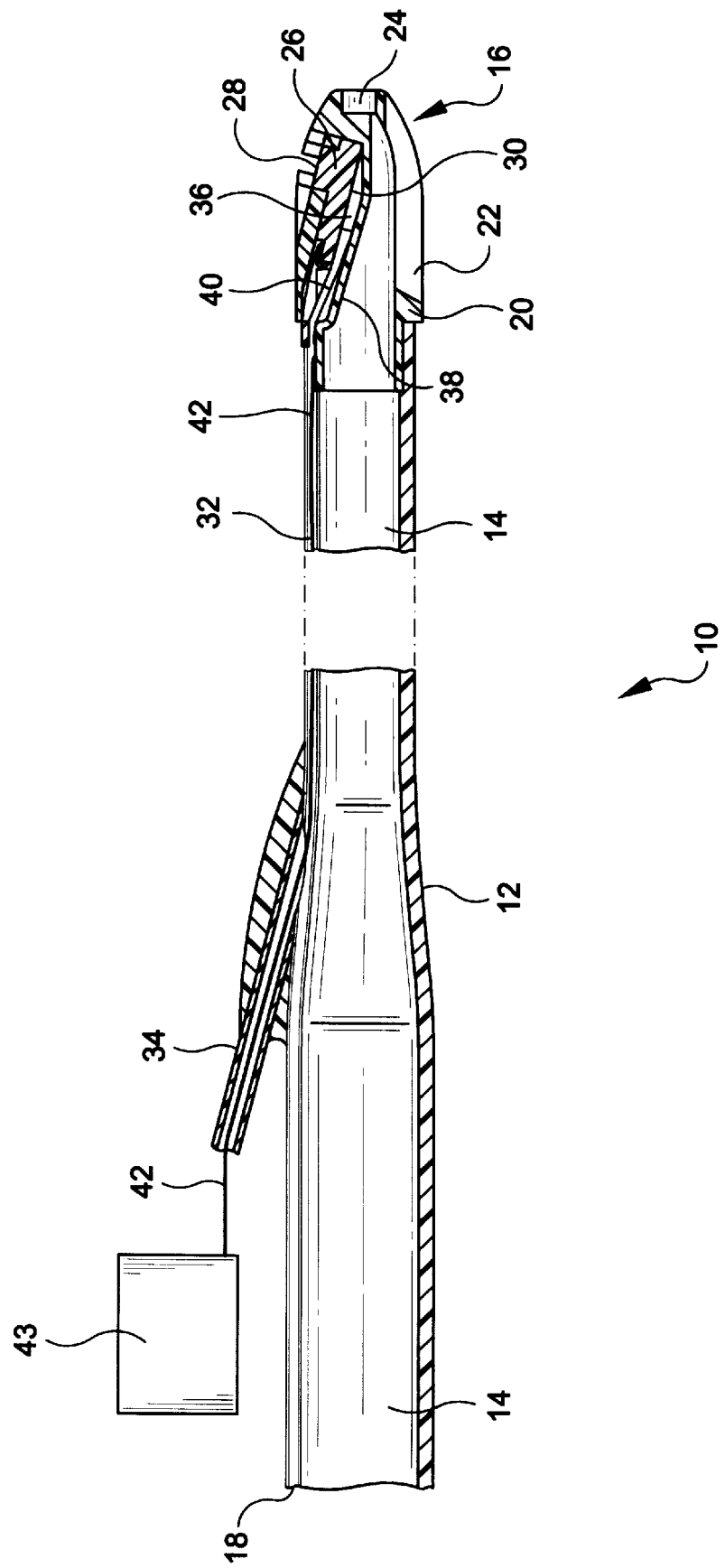
FIG. 1 is a sectional view, partially schematic, of a pressure tip cannula constructed in accordance with the present invention.

Referring now to FIG. 1, there is shown a side cross-sectional view of a pressure tip cannula 10 constructed in accordance with the present invention. As can be seen, the cannula 10 comprises a length of flexible tubing 12 having a central bore 14 that extends from the distal end 16 through to the proximal end 18. As used herein, the distal end 16 shall refer to the end of the cannula 10 that is intended to be inserted into the heart of the patient to remove blood therefrom and the proximal end 18 shall refer to the end of the cannula 10 that remains external to the patient and which is adapted to be connected to the pump (not shown) that draws blood through the cannula 10 from the heart.

Typically, cannula 10 is comprised of a plastic material that is of sufficient flexibility so as to be relatively maneuverable as it is positioned by the user in the desired location withdrawing blood from the heart, such as in the left ventricle or atrium. Although various size cannulas can be used, it is preferred in the use of the cannula for bypass surgery that the cannula be in the range of about 36 French so that the central bore 14 is sufficiently large to remove the flow of blood from the heart needed to divert flow otherwise passing through the heart during a bypass operation.

At the distal end 16 of the cannula 10, there is formed a cannula tip 20 that, as explained, is actually placed in the particular chamber of the patient's heart to withdraw the blood. In normal bypass surgery, that chamber would be the left ventricle or atrium and the blood returned via the ascending aorta. As shown, the cannula tip 20 includes a plurality of slots 22 (only one of which is shown) that allow the suctioning of the blood from the heart chamber and a further central opening 24 may be formed in the cannula tip 20 so that the blood enters the cannula tip 20 and proceeds through the central bore 14 to the proximal end 18 At that proximal end 18, some connection is provided to direct the blood to the heart pump for recirculation back to the heart.

At or adjacent to the distal end 16, there is positioned a pressure sensor 26 in the form of an electronic piezoresistive chip that is specially adapted to be an economical disposable sensor for such purpose. Such sensors are readily available commercially, from companies such as Motorola and Lucas Novasensor and are currently in use to sense certain pressures of a patient. The sensor is a piezoresistive crystal in the form of a Wheatstone bridge and the flexing of the crystal alters its resistance. Accordingly, the pressure sensor 26 is normally placed intermediate the chamber containing the fluid to be sensed and a chamber having a reference pressure, such as atmospheric pressure. Accordingly the piezoresistive chip has a pressure sensing side and a reference pressure side such that the flexing changes the resistance of the chip. That change in resistance is detected with conventional instruments and converted to a measurement of the differential pressure. In general, the reference pressure side is positioned in a chamber that is vented to atmosphere so that the pressure reading is an absolute value with respect to the ambient pressure.

As shown in FIG. 1, therefore the pressure sensor 26 is located in the cannula tip 20 such that its pressure sensing side 28 is facing the external, outer portion of the distal end 16 of the cannula tip 20 and therefore sensing the pressure of the blood in the particular heart chamber of the patient. As will be seen, therefore, by having the pressure sensing side 28 facing the outer portion of the cannula tip 20 and not the central bore 14, the pressure measurement is basically free from the inaccuracies that occur due to the dynamics of the flow of blood through the cannula 10.

The pressure sensor has its reference pressure side 30, in the preferred embodiment, vented to atmosphere through a lumen 32 formed in the wall of the cannula 10 and further through a tube 34 to the ambient atmosphere. An enclosed reference chamber 36 is formed to isolate the reference pressure side 30 of the pressure sensor 26 from the central bore 14 and, therefore, from the effects of the blood flowing through that central bore 14 by means of a wall 38 formed in the cannula tip 20. Accordingly that enclosed reference chamber 36 is formed between the wall 38 and the reference pressure side 30 of the pressure sensor 26. A minute tube 40 can be used to communicate the enclosed reference chamber 36 to the lumen 32 for convenience of manufacture and assembly of the cannula tip 20 to the flexible tubing 12.

In this manner, the reference pressure side 30 of the pressure sensor 26 is vented to atmosphere and thus the pressure on the pressure sensing side 28 of the pressure sensor 26 will provide the absolute pressure of the blood in the particular chamber of the heart when the cannula 10 is positioned but not be affected by the dynamic flow of the blood. In addition, by the positioning of the pressure sensor 26 isolated from the central bore 14 by means of the wall 38, the pressure sensor 26 does not impede the flow of the blood.

Various wires 42 connect the pressure sensor 26 to an electronic readout device 43, shown schematically in FIG. 1. That electronic readout device is a conventional instrument currently widely used to convert the change of resistance in the piezoresistive device to a reading of differential pressures between the enclosed reference chamber 36 and the particular chamber of fluid that is in contact with the pressure sensing side 28 of the device.

Figure 3:
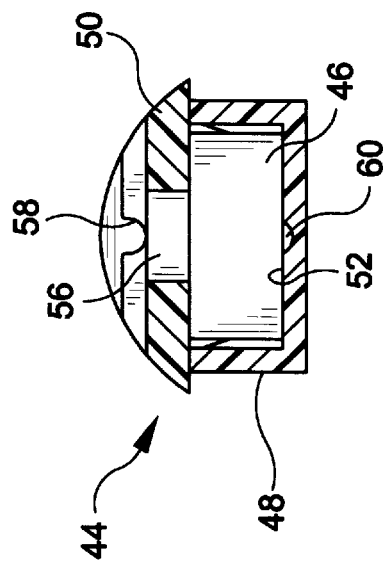
FIG. 3 is a end cross sectional view of the sensor assembly of FIG. 2.
Figure 2:
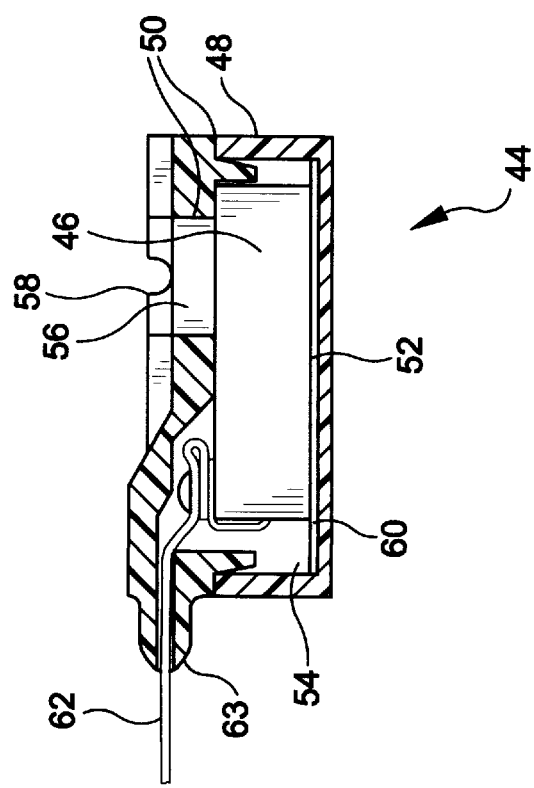
FIG. 2 is a side cross sectional view of a sensor assembly that is used in the pressure tip cannula of FIG. 1.

Turning now to FIGS. 2 and 3, there is show a side cross sectional view and an end cross sectional view of a pressure sensor assembly 44 that is usable with a further embodiment of the present invention. In this embodiment, the pressure sensor 46, again which is a commercially available piezoresistive device, is enclosed and is fitted within a base 48 having a cover 50 fitted thereto to enclose the pressure sensor 46. In this embodiment, the reference pressure side 52 of the pressure sensor 46 is positioned so as to be at the bottom of the base 48 and which lies within a closed reference pressure chamber 54 within the pressure sensor assembly 44.

The pressure sensing side 56 of the pressure sensor 46 faces outwardly and is sealed by the cover 50 to isolate it from the reference pressure chamber 54. In the top of the cover 50, there is formed a groove 58 which may be in the form of a cross, so that the pressure sensing side 56 of the pressure sensor 46 maintains a clear channel even if the pressure sensor assembly 44 contacts the inner wall of the heart. In such event, the groove 58 will still enable the pressure sensor 46 to have a channel to the blood within the heart even if the pressure sensor 46 is in that direct contact with the inner wall of the heart. A further groove 60 is formed in the base 48, along the bottom thereof, such that a clear channel is provided for formation of the reference pressure chamber 54 and so that the reference pressure side 52 of the pressure sensor 46 is not sealed or pressed against the surface of the bottom of the base 48 so as to occlude or impede the operation of the reference pressure side 52 of pressure sensor 46.

Again, wires 62 for making an electrical connection with the pressure sensor 46 are provided and which pass through an opening 63 in the cover 50 to pass further through a lumen to be accessible exterior of the pressure sensor assembly 44.

Figure 5:
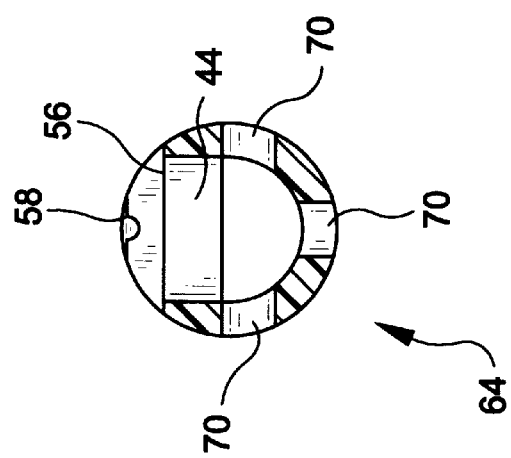
FIG. 5 is a end cross sectional view of the cannula of FIG. 4.
Figure 4:
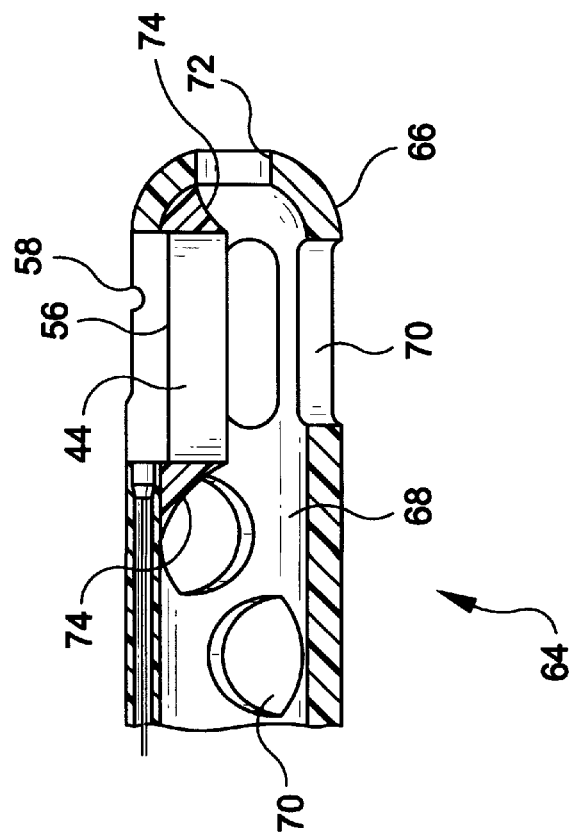
FIG. 4 is an enlarged schematic view of a further embodiment of a cannula constructed in accordance with the present invention.

Turning now to FIGS. 4 and 5, there is shown a side cross sectional view and an end cross sectional view of a cannula 64 using the pressure sensor assembly 44 shown in FIGS. 2 and 3. As shown, the pressure assembly 44 is fitted within the wall of the distal end 66 of the cannula 64 and the cannula 64 has a central bore 68 through which the blood flows as it is drawn from the patient's heart through a plurality of openings 70 in the side wall of the cannula 64 and a further central opening 72 at the far distal end 66 of the cannula 64. The pressure sensor assembly 44 may be secured to the wall of the cannula 64 by a variety of means, one of which is with a fillets 74 of an adhesive material to secure the pressure sensor assembly 44 as well as to streamline the passage of blood through the central bore 68.

Accordingly, as can be seen by FIGS. 4 and 5, the pressure sensing side 56 of the pressure sensor assembly 44 faces external of the wall of cannula 64 such that it can sense the pressure of the heart chamber within which it is positioned during use and not be affected by the dynamics of the blood passing through the central bore 68 as it is being withdraw from that heart chamber.

Figure 6:
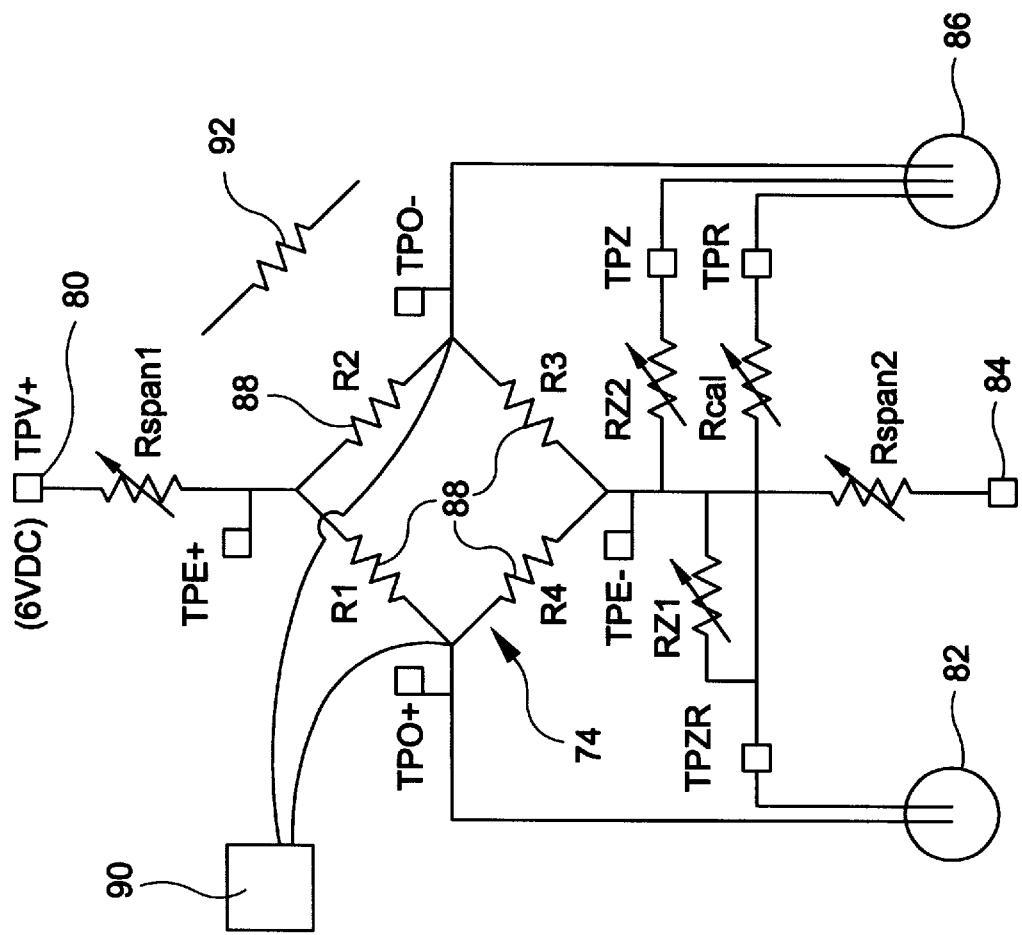
FIG. 6 is an electrical schematic showing the application of the present invention with respect to temperature compensation of a pressure sensor.

Turning now to FIG. 6, there is shown an electrical schematic of the Wheatstone bridge 74 that is basically formed in the piezoresistive chip used with the present invention. As is conventional, all four of the resistors change resistance with a change in the differential pressure across the piezoresistive chip itself. Two of the resistors increase with an increase of pressure on the sensing side and two of the resistors decrease in resistance with that increase in pressure. The change in resistance causes a change in balance of the Wheatstone bridge 76 that is detected by conventional instruments and converted to a reading of pressure to the user. The remaining components shown in FIG. 6 are all conventionally supplied in the commercial piezoresistive chips readily available from commercial suppliers, such as Motorola.

As shown, the Wheatstone bridge has four terminals, identified as terminals 80, 82, 84 and 86 and each terminal, of course includes a resistor 88 between the terminal as is normal in a Wheatstone bridge. In the normal zeroing of the Wheatstone bridge, a voltage, such as 6 volts is applied to the terminals 80 and 84 and, if the bridge is balanced, the meter 90, generally a galvanometer, will show that the signal is zero. In carrying out the present invention, however, a compensation is made to the pressure sensor so that it is compensated to the patient body temperature, that is, the pressure sensor is compensated to be at 36 degrees Centigrade, or body temperature. To achieve that compensation, the pressure sensor is placed in an environment at that temperature for a sufficient time to assure that the pressure sensor has reached the temperature of that environment. A reading of the meter 90 is again taken to determine the magnitude of the offset and to determine whether the offset is negative or positive. A further resistor, shown schematically as 92, is then added to the Wheatstone bridge to zero the meter 90 at that temperature.

The resistor 92 is added between terminals 84 and 86 if the reading of the meter 90 is negative and between terminals 80 and 86 if the reading is positive. The value of the resistance may be chosen by trial and error or by experience depending on the magnitude that is shown by the meter 90 to be off set from the zero point. In any event, with the addition of the resistor 92, the pressure sensor is compensated to 36 degrees Centigrade and is zeroed at that temperature.

Therefore, when the cannula is actually placed into the patient's body and the distal end located in the patient's heart, which is at 36 degrees Centigrade, the pressure sensor will be zeroed at that temperature and thus not have the inaccuracy normally inherent in such pressure sensor by the zero offset resulting from the temperature change when the cannula is placed into the patient's body.

For example, the typical sensor has a zero shift specification of +/−0.30 mmHg /degree C. By standardizing the sensors at body temperature, (36 degrees Centigrade) the error in measuring the pressure +/−4.5 mmHg is reduced to +/−1.0 mmHg.

While the foregoing presents a working embodiment of the invention, there are others embodiments that will be obvious to those skilled in the art. The invention is not limited to the embodiments specifically described but is to be interpreted only in conjunction with the scope of the appended claims and their functional equivalents.

I claim:

1. A cannula comprising:

a main body portion defining a fluid flow lumen extending therethrough;

a pressure sensing chamber located in the main body portion and having an opening through the main body portion but isolated from the fluid flow lumen;

a pressure sensor zero compensated to 36 degrees Centigrade disposed in the pressure sensing chamber; and a cover over the opening and the pressure sensor, the cover defining a groove therein in communication with the pressure sensor.

2. The cannula of claim 1 wherever the pressure sensing chamber includes a base on which the pressure sensor is located and wherein the base defines a groove in communication with the pressure sensor.

* * * * *